(12) United States Patent
Freyssinet et al.

(10) Patent No.: US 6,229,065 B1
(45) Date of Patent: *May 8, 2001

(54) **PRODUCTION OF PLANTS RESISTANT TO ATTACKS BY *SCLEROTINIA SCLEROTIORUM* BY THE INTRODUCTION OF A GENE ENCODING AN OXALATE OXIDASE**

(75) Inventors: Georges Freyssinet, St Cyr au Mont d'Or; Alain Sailland, Lyons, both of (FR)

(73) Assignee: Rhone-Poulenc Agrochimie (FR)

( * ) Notice: Subject to any disclaimer, the term of this patent is extended or adjusted under 35 U.S.C. 154(b) by 0 days.

This patent is subject to a terminal disclaimer.

(21) Appl. No.: 08/400,006

(22) Filed: Mar. 6, 1995

Related U.S. Application Data

(62) Continuation of application No. 08/207,105, filed on Mar. 8, 1994, now abandoned, which is a continuation of application No. 07/941,135, filed as application No. PCT/FR92/00195 on Mar. 4, 1992, now abandoned.

(30) Foreign Application Priority Data

Mar. 5, 1991 (FR) .................................................. 91 02874

(51) Int. Cl.[7] ........................... C12N 15/82; C12N 15/29; A01H 1/00

(52) U.S. Cl. ......................... 800/279; 800/278; 435/69.2; 435/69.8; 435/468; 536/23.6

(58) Field of Search ................................ 435/69.2, 172.3, 435/320.1, 468, 69.8; 800/200, 205, 250, DIG. 15, 278, 279, 298, 301; 935/11, 22; 47/58, 58.07; 536/23.6

(56) References Cited

U.S. PATENT DOCUMENTS 5,866,778 * 2/1999 Hartman et al. ..................... 800/205

OTHER PUBLICATIONS

Dumas, B., G. Freyssinet, K.E. Pallett. Tissue specific expression of germin–like oxalate oxidase during development and fungal infection of barley seedlings. Plant Physiol. 107: 1091–1096, 1995.*

Thompson, C., J.M. Dunwell, C.E. Johnstone, V. Lay, J. Ray, M. Schmitt, H. Watson, and G. Nisbet. Degradation of oxalic acid by transgenic oilseed rape plants expressing oxalate oxidase. Euphytica. 85:169–172, 1995.*

Zhang, Z., D.B. Collinge, and H. Thordal–Christensen. Germin–like oxalate oxidase, a $H_2O_2$–producing enzyme, accumulates in barley attacked by the powdery mildew fungus. The Plant Journal. 8: 139–145, 1995.*

Dratewka–Kos et al. 1989. The Journal of Biological Chemistry. 264(9): 4896–4900.*

Lane et al. 1991. The Journal of Biological Chemistry. 266(16):10461–10469.*

* cited by examiner

*Primary Examiner*—David T. Fox
*Assistant Examiner*—Melissa L. Kimball
(74) *Attorney, Agent, or Firm*—Burns, Doane, Swecker & Mathis, L.L.P.

(57) ABSTRACT

The present invention provides a DNA sequence encoding an oxalate oxidase. The oxalate oxydase may be used for the resistance of plants to diseases caused by Sclerotinia sp. It may be provided by a chimeric gene and a vector containing the coding sequence. It may be used to confer on plants an increased resistance to diseases caused by Sclerotinia sp.

8 Claims, 1 Drawing Sheet

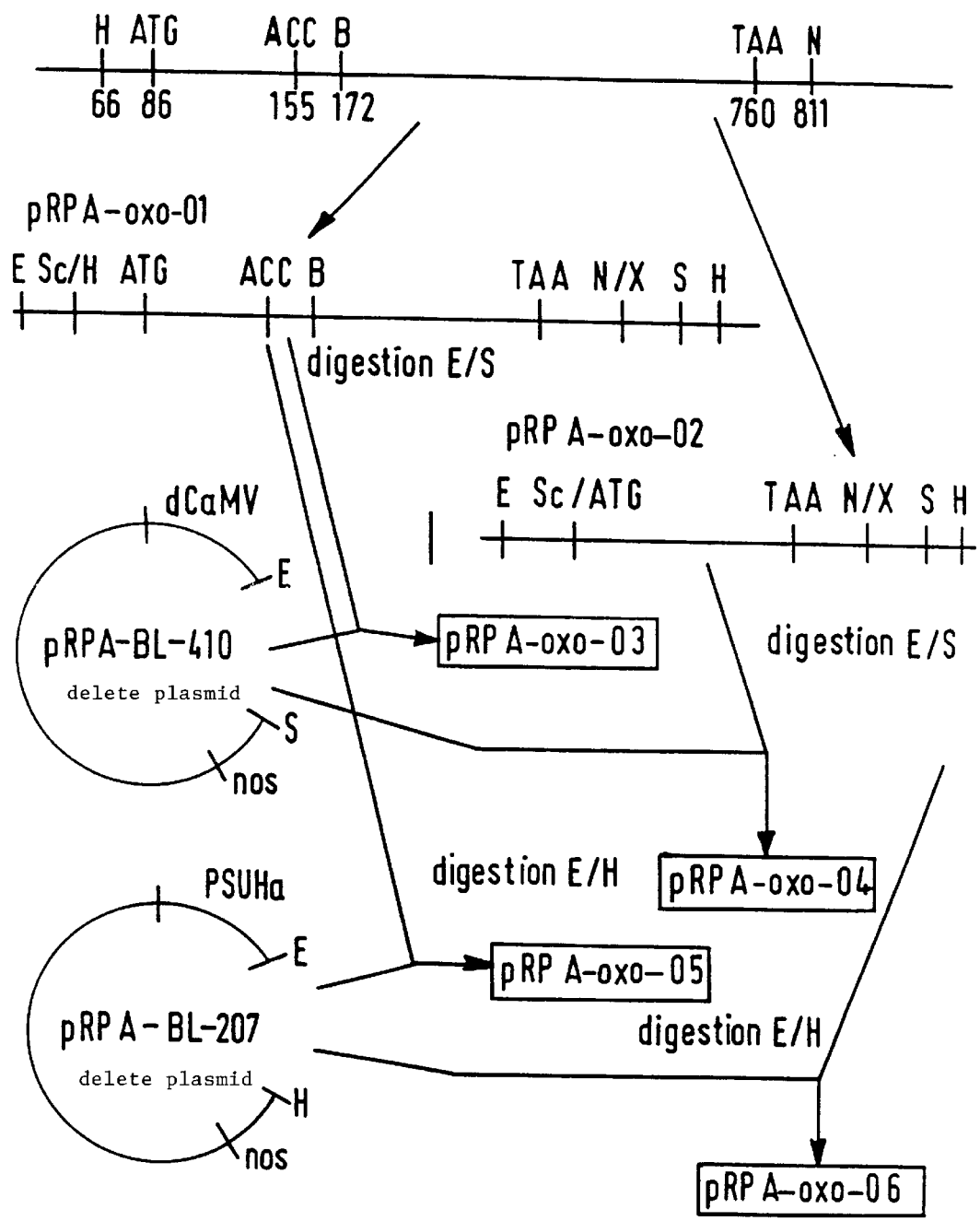

PRODUCTION OF PLANTS RESISTANT TO ATTACKS BY SCLEROTINIA SCLEROTIORUM BY THE INTRODUCTION OF A GENE ENCODING AN OXALATE OXIDASE

This application is a continuation of application Ser. No. 08/207,105, filed Mar. 8, 1994, now abandoned, which is a continuation of application Ser. No. 07/941,135, filed Dec. 3, 1992, now abandoned, which is a 371 of PCT/FR92/00195, filed Mar. 4, 1992.

SUMMARY OF THE INVENTION

1. Field of the Invention

The subject of the present invention is a gene encoding an oxalate oxidase, the protein encoded by this gene, the chimeric genes comprising this gene and their use for transformation of dicotyledonous plants in order to confer on those plants a resistance to fungal diseases.

2. Description of the Related Art

Sclerotiniosis is a major fungal disease which affects a large number of dicotyledons. The causative agent, *Sclerotinia sclerotiorum* is a polyphagous fungus which exhibits little host specificity.

The fungus can attack the plant either directly at the level of the stem, or at the level of the leaves and then spread to the stem, or at the level of the floral capitulum. In the first two cases, the plant withers from disruption to food supply. In the last case, the flower withers, damaging the harvest.

The fungus produces lytic enzymes which degrade the cell wall of the infected plant and promote its development in the plant. These enzymes play an important role in pathogenicity, but do not appear to be sufficient. This fungus also produces oxalic acid (Godoy et al. (1990) *Physiol. Molec. Plant. Pathol.* 37: 179–181). This oxalic acid causes a decrease in pH in the infected tissues, promoting hydrolysis of the cell wall by the lytic enzymes. A reduction in the production of oxalic acid or degradation of this oxalic acid should permit a slowing-down or even an inhibition of the development of the fungus.

In order to develop a Sclerotinia resistant plant, the strategy of detoxification of oxalic acid may be used. The degradation of this acid will limit the decrease in intracellular pH of the plant tissue attacked, the lytic enzymes will thereby be functioning at a value too far-removed from their optimum pH to be really active and efficient. This will lead to a decrease in the pathogenicity of the fungus.

Oxalate oxidase which catalyses the following reaction:

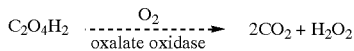

may be used to achieve this objective.

Oxalate oxidase is isolated from various plants, generally from monocotyledons (Pieta et al. (1982) *Preparative Biochemistry* 12(4):341–353): the protein may for example be purified from barley using conventional chromatographic techniques (Sephadex G-75 filtration gels and MonoQ ion exchange gels, Pharmacia), by monitoring the enzymatic activity according to the following calorimetric procedure (Obzansky and Richardson (1983) *Clin. Chem.* 29(10):1815–1819):

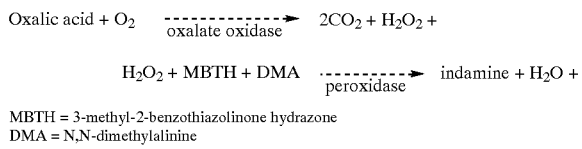

MBTH = 3-methyl-2-benzothiazolinone hydrazone
DMA = N,N-dimethylalinine

This has made it possible to purify a protein which, on acrylamide gel under denaturing conditions, has a molecular mass of 26,000 daltons. Part of the purified oxalate oxidase was used to obtain rabbit anti-oxalate oxidase antibodies; the remainder of the protein was used to carry out the sequencing of the native protein (N-terminal) or, after cyanogen bromide cleavage, the sequencing of certain internal peptides. The results obtained are as follows:

N-terminal [SEQ ID NO.1]: IDPDPLQDF-VADLDGKAVSVNGH
S [SEQ ID NO.2]
Internal peptide No.2 [SEQ ID NO.2]: HFQFNVGK-TEAY cDNA Comparison of the peptide sequences described above with the data contained in the protein library Swiss-Prot enabled us to identify a wheat protein called Germine and published in 1989 by Dratewka-kos et al. Experiments were carried out and they enabled us to determine that the CDNA published by the authors encodes a protein of 201 amino acids which exhibits an oxalate oxidase activity. For the rest of the description of the experiments presented in this patent, we will use the nucleotide numbering in FIG. 2 in the article by the authors published in J. Biol. Chem., 264, 4896–4900.

The sequence of this cDNA which is set forth in SEQ ID NO:6, is 1075 nucleotides in length with an untranslated 5' of 85 residues, an open reading frame of 672 nucleotides (from position 86 to 757) and an untranslated 3' of 318 residues.

Comparison of the protein sequence deduced from the CDNA sequence with that obtained by sequencing the native protein shows that the CDNA encodes not only mature oxalate oxidase but also a signal peptide of 23 amino acids in the N-terminal part. Oxalate oxidase is therefore synthesized in the form of a preprotein (signal peptide plus mature peptide) which undergoes maturation by removal of the signal peptide in order to release the mature active enzyme.

In the following, we will use either the part encoding the preprotein (nucleotides 86 to 757), or only that part encoding the mature protein (from position 155 to 757). In the latter case, an AUG codon (encoding a methionine) should be placed before the ACC codon (encoding threonine, the first amino acid of the mature protein).

The attacks on plants by *Sclerotinia sclerotiorum* being essentially through the stem or the plant, it is advantageous to be able to express oxalate oxidase either in chlorophyllous tissues, and for that the promoter of the small subunit of ribulose 1,5-di-phosphate carboxylase of *Helianthus annuus* (SSUHa, Waksman et al. (1987) *Nucl. Acid Res.* 15:7181) may be used, or in the various tissues of the plant, and for that we will use the ubiquitous promoter of the 35S RNA of the cauliflower mosaic virus (CAMV 35S) part of which was duplicated and which is called "double CaMV".

SUMMARY OF THE INVENTION

The chimeric genes according to the invention may be for example constructed from the following elements:

BRIEF DESCRIPTION OF THE DRAWING

FIG. 1. Obtention procedure of the four chimeric genes from both coding genes, pRPA-oxo-01 and pRPA-oxo-02H, HindIII ; B, BstN; N, NheI; E, EcoRI; Sc, SacI; S, SalI and X, XbaI.

A. Double CaMV promoter followed by that part of the oxalate oxidase CDNA encoding the pre-protein (signal peptide plus mature peptide) and the terminator "nos" obtained from the pTi 37 nopaline synthase gene (Bevan et al., 1983).
B. Double CaMV promoter followed by that part of the oxalate oxidase CDNA encoding only the mature protein followed by the terminator "nos".
C. Gene identical to "A" but with the promoter of the small subunit of sunflower ribulose 1,5-diphosphate carboxylase (SSUHa) in place of the double CaMV.
D. Gene identical to "B" but with the promoter of the SSUHa in place of the double CAMV.

Each chimeric gene is introduced into the plant cell by a system using *Agrobacterium* or any other system otherwise known for transforming plant cells. Plants are regenerated from these transformed cells. They exhibit an increased tolerance to *Sclerotinia sclerotiorum*.

DETAILED DESCRIPTION OF THE INVENTION

EXAMPLE 1

Preparation of Two Coding Sequences:

Preprotein: it is obtained from the cDNA described above, digested with HindIII (in position 66). The cohesive end obtained is made blunt by treating with Klenow polymerase. This DNA is then digested with NheI (in position 811).

The plasmid pUC 19 (Yanisch-Perron et al., 1985) is digested in parallel with SacI.

The cohesive end obtained is made blunt by treating with Klenow polymerase. The plasmid is then digested with XbaI (compatible with NheI).

The cDNA fragment and plasmid prepared above are ligated. The new plasmid thus obtained is called pRPA-oxo-01 and its map is presented in FIG. 1.

B. Mature protein: it is obtained from the CDNA described above after digestion with BstNI (in position 173). The fragment obtained and the linker of the sequence [SEQ ID NO.3]:

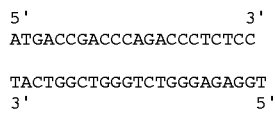

are ligated. This leads to a modification of the N-terminal sequence of the mature protein which passes from TDPDPLQ [SEQ ID NO.4] to MTDPDPLQ [SEQ ID NO.5].

This CDNA fragment is then digested with NheI (in position 811) so that it can then be ligated with the plasmid pUC19 prepared as described in the paragraph above. The new plasmid thus formed is called pRPA-oxo-02 and its map is presented in FIG. 1.

EXAMPLE 2

Preparation of the Chimeric Genes:

a. Preparation of the Vectors Containing the Promoter and the Terminator Nos;

example double CAMV: this vector is obtained from the plasmid pRPA-BL-410 obtained in the following manner:

"Transit Peptide of the SSU of Maize RuBisCO/AroA Gene" Fusion:

The transit peptide of the SSU of the maize RuBisCO gene is derived from an EcoRI-SphI fragment of 192-bp; it is obtained from the cDNA corresponding to the SSU gene of the maize RuBisCO gene described by Lebrun et al. (1987) *Nucl. Acid Res.* 15:4360 with an NcoI site spanning the initiation codon for translation and an SphI site corresponding to the cleavage site of the transit peptide.

The translational fusion between the maize transit peptide and the bacterial EPSPS gene is obtained by treating the SphI end with the bacteriophage T4 polymerase and by ligating it with the Klenow polymerase-treated NcoI end of the AroA gene of pRPA-BL 104 recut with EcoRI.

Transit Peptide of the SSU of Maize RuBisCO/Sequence of 22 Amino Acids of the Mature Part of the SSU of Maize RuBisCO/AroA Gene Fusion:

In a similar fashion, an EcoRI-HindII fragment of 228 bp of the cDNA of the SSU of maize RuBisCO gene is ligated with the Klenow polymerase-treated NcoI end of the AroA gene of pRPA-BL 104 and recut with EcoRI. A translational fusion is obtained between the transit peptide of the SSU of maize RuBisCO, the 22 amino acids of the mature part of the SSU of maize RuBisCO and the bacterial EPSPS gene.

Transit Peptide of the SSU of Sunflower RuBisCO:

The fragment is obtained from the cDNA isolated by Waksman and Freyssinet (1987) (*Nucl. Acid Res.* 15:1328). A SphI site was created according to the method of Zoller and Smith (1984) (*Method Enzymol.* 154:329) at the cleavage site of the transit peptide. The transit peptide of the SSU of sunflower RuBisCO thus obtained is an EcoRI-SphI fragment of 171 bp.

Transit Peptide of the SSU of Sunflower RuBisCO/Sequence of 22 Amino Acids of the Mature Part of the SSU of Maize RuBisCO/AroA Gene Fusion:

The construct containing the transit peptide of the SSU of maize RuBisCO/sequence of 22 amino acids of the SSU of maize RuBisCO of the mature part of the maize gene fusion was cut with EcoRI-SphI of 171 bp corresponding to the transit peptide of the SSU of the said sunflower RuBisCO gene. The resulting construct exhibits a substitution of the EcoRI-SphI fragments and is a translational fusion, "transit peptide of the SSU or sunflower RuBisCo/sequence of 22 amino acids of the mature part of the SSU of maize RuBisCO/AroA gene.

The EcoRI-SalI fragment was ligated with the SalI-SstI fragment containing the 3' nos sequence and the right end of the T-DNA. The resulting EcoRI-SstI fragment comprising "transit peptide of the SSU of sunflower RuBisCO/sequence of 22 amino acids of the mature part of the SSU of maize RuBisCO/AroA gene/3' nos/T-DNA right end" is substituted for the EcoRI-SstI fragment containing the right end of the T-DNA of the plasmid 150 A alpha 2 containing the double CaXV promoter. The transcriptional fusion "double CaMV/transit peptide of the SSU of sunflower RuBisCO/sequence of 22 amino acids of the mature part of the SSU of maize RuBisCO/AroA gene/3'nos" in the vector 150 A alpha 2 was called pRPA-BL 294.

Transit Peptide of the SSU of Sunflower RuBisCO/Sequence of 22 Amino Acids of the SSU of Maize RuBisCO/Transit Peptide of the SSU of Maize RuBisCO/AroA Gene" Fusion:

The construct above is cut with NcoI-HindIII releasing the AroA gene. It is then ligated with a 1.5-kbp NcoI-HindIII fragment containing the "transit peptide of the SSU of maize RuBisCO/AroA gene" fusion. The resulting construct exhibits a substitution of the NcoI-HindIII fragments and is a translational fusion "transit peptide of the SSU of sunflower RuBisCO/sequence of 22 amino acids of the SSU of RuBisCO of the mature part of the maize gene/transit peptide of the SSU of maize RuBisCO/AroA gene".

The EcoRI-SalI fragment was ligated with the SalI-SstI fragment containing the 3' nos sequence and the right end of the T-DNA. The resulting EcoRI-SstI fragment comprising "transit peptide of the SSU of sunflower RuBisCO/sequence of 22 amino acids of the SSU of RuBisCO of the mature part of the maize gene/transit peptide of the SSU of maize RuBisCO/AroA gene/ 3'nos/T-DNA right end" is substituted for the EcoRI-SstI fragment containing the right end of T-DNA of the plasmid 150 A alpha 2 containing the double CaMV promoter. The transcriptional fusion "double CaMV/ transit peptide of the SSU of sunflower RuBisCO/ sequence of 22 amino acids of the SSU of RuBisCO of the mature part of the maize gene/transit peptide of the SSU of maize RuBisCO/AroA gene/3'nos" in the vector 150 A alpha 2 was called pRPA-BL 410. This plasmid is digested with EcoRI and SalI in order to remove the structural gene "optimised transit peptide-mature EPSPS encoding region", pRPA-BL-410 deleted (see FIG. 1).

Example SSUHa: this vector is obtained from the plasmid pRPA-BL-207 (described in European Patent Application 0,337,899) which is digested with EcoRI and HindIII in order to remove the nitrilase-encoding region, pRPA-BL-207 deleted (see FIG. 1).

b. Construction of chimeric genes:

pRPA-oxo-03: it is obtained by digesting pRPA-oxo-01 with EcoRI and SalI. The fragment obtained, which encodes the preprotein, is then inserted between the EcoRI and SalI sites downstream of the double CaMV and upstream of the terminator nos respectively.

pRPA-oxo-04: it is obtained by digesting pRPA-oxo-02 with EcoRI and SalI. The fragment obtained, which encodes the mature protein, is then inserted between the EcoRI and SalI sites downstream of the double CaMV and upstream of the terminator nos respectively.

pRPA-oxo-05: it is obtained by digesting pRPA-oxo-01 with EcoRI and HindIII. The fragment obtained, which encodes the preprotein, is then inserted between the EcoRI and HindIII sites downstream of the double SSUHa and upstream of the terminator nos respectively.

pRPA-oxo-06: it is obtained by-digesting pRPA-oxo-02 with EcoRI and HindIII. The fragment obtained, which encodes the mature protein, is then inserted between the EcoRI and HindIII sites downstream of the SSUHa promoter and the terminator nos respectively.

TABLE 1

Schematic representation of the four chimeric genes:

| Identification | Promoter | Oxalate oxidase encoding region | Terminator |
|---|---|---|---|
| pRPA-oxo-03 | dCaMV | preprotein | nos |
| pRPA-oxo-04 | dCaMV | mature | nos |
| pRPA-oxo-05 | SSUHa | preprotein | nos |
| pRPA-oxo-06 | SSUHa | mature | nos |

EXAMPLE 3

Production of Transgenic Colzas:

a. Transformation

Each vector, as described above, is introduced into the nononcogenic *Agrobacterium tumefaciens* strain EHA 101 (Hood et al. (1986) *J. Bacteriol.* 168: 1291–1301) carrying the cosmid PTVK 291 (Komari et al. (1986) *J. Bacteriol.* 166: 88–94).

The method of transforming colza, Westar variety, is essentially based on that described by Boulter et al. (1990) (*Plant Sci.* 70:91–99), using a bacterial concentration of $2.5 \times 10[]9$ per ml (OD 600 nm=1).

b. Regeneration

The method of regeneration is essentially based on that described by Boulter et al. (1990) (*Plant Sci.* 70:91–99). The plants are rooted on the medium of De Block et al. (1989) (*Plant Sci.* 1:694–701). They are then brought to the flowering stage in a greenhouse.

EXAMPLE 4

Measurement of the Resistance of Colza to *Sclerotinia sclerotiorum*:

In Vitro:

Foliar discs: the resistance is measured by weighing the mass of three foliar discs after growing for 11 days on a Murashige and Skoog (MS) medium with hormones, supplemented with 1 mM of oxalic acid.

Under these conditions, it is observed that for the foliar discs obtained from colzas (western varity) modified using one of the chimeric genes, pRPA-oxo-03, pRPA-oxo-04, pRPA-oxo-05 and pRPA-oxo-06, the mass of the foliar discs increases substantially whereas, in the case of the foliar discs obtained from unmodified colzas, the mass stagnates or even decreases.

Root elongation: the resistance is also measured in vitro by measuring root elongation after growing for two days on water supplemented with 5 mM of oxalic acid. It is observed, in this case, that the roots of colza plants modified with one of the chimeric genes, pRPA-oxo-03, pRPA-oxo-04, are capable of growing and increasing in length, whereas the roots of unmodified colzas show no growth under these conditions.

In Vivo:

The resistance in vivo is measured in a greenhouse after contaminating colza plants obtained from the regeneration, as soon as the first flowers appeared, either by depositing *S. sclerotiorum* spores on the petals, the infection of the leaves thereby occurring naturally during defloration, or by directly depositing mycelium or a mycelium-impregnated petal on the leaves. The plants modified by one of the chimeric genes, pRPA-oxo-03, pRPA-oxo-04, pRPA-oxo-05 and pRPA-oxo-06 do not allow the fungus to develop and do not exhibit any symptom of rot characteristic of sclerotiniose, whereas the unmodified plants are rapidly overcome by rot characteristic of the development of *Sclerotinia sclerotiorum*.

What is claimed is:

1. A method of conferring on plants resistance to sclerotiniosis comprising transforming said plants with a DNA sequence encoding an oxalate oxidase pre-protein comprising an oxalate oxidase signal peptide and an oxalate oxidase mature peptide and recovering sclerotiniosis-resistant plants.

2. The method of claim 1, wherein said oxalate oxidase pre-protein is the wheat germin pre-protein.

3. The method of claim 2, wherein the DNA sequence encoding an oxalate oxidase pre-protein encodes an oxalate oxidase signal peptide and an oxalate oxidase mature protein comprising the amino acid sequence of SEQ ID NO: 1.

4. A method of reducing oxalic acid in plants comprising transforming said plants with a DNA encoding an oxalate oxidase pre-protein comprising of an oxalate signal peptide and an oxalate oxidase mature peptide and recovering transformed plants which have reduced oxalic acid content.

5. The method of claim 4, wherein said oxalate oxidase pre-protein is the wheat germin pre-protein.

6. The method of claim 5, wherein said DNA sequence encoding an oxalate oxidase pre-protein encodes an oxalate oxidase signal peptide and an oxalate oxidase mature protein comprising the sequence of SEQ ID NO:1.

7. The method of claim 6, wherein the DNA has a sequence selected from the group consisting of:

a) the DNA sequence of SEQ ID NO: 6 and b) the DNA sequence from nucleotides 86 to 757 of SEQ ID NO:6.

8. The method of claim 3, wherein said DNA sequence encoding an oxalate oxidase pre-protein has a sequence selected from the group consisting of:

a) the DNA sequence of RPA-SEQ ID NO: 6 and b) the DNA sequence from nucleotides 86 to 757 of SEQ ID NO:6.

* * * * *

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (ix) OTHER INFORMATION: Xaa at the first position can be Ile (I) or
        Ser (S).
        (A) NAME/KEY: Peptide
        (B) LOCATION: 1
        (D) OTHER INFORMATION:

(xi) SEQUENCE DESCRIPTION: SEQ ID NO: 1:

Xaa Asp Pro Asp Pro Leu Gln Asp Phe Val Ala Asp Leu Asp Gly Ly
1               5                   10                  15

Ala Val Ser Val Asn Gly His
            20

(2) INFORMATION FOR SEQ ID NO: 2:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 2:

His Phe Gln Phe Asn Val Gly Lys Thr Glu Ala Tyr
1               5                   10

(2) INFORMATION FOR SEQ ID NO: 3:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: misc_feature
        (B) LOCATION: 23
        (D) OTHER INFORMATION: /note= "5'T has no complimentary base."

(xi) SEQUENCE DESCRIPTION: SEQ ID NO: 3:

TGGAGAGGGT CTGGGTCGGT CAT                                    23

(2) INFORMATION FOR SEQ ID NO: 4:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

Thr Asp Pro Asp Pro Leu Gln
1               5

(2) INFORMATION FOR SEQ ID NO: 5:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 5:

Met Thr Asp Pro Asp Pro Leu Gln
1               5

(2) INFORMATION FOR SEQ ID NO: 6:

(i) SEQUENCE CHARACTERISTICS:
            (A) LENGTH: 1075
            (B) TYPE: nucleic acid
            (C) STRANDEDNESS: single
            (D) TOPOLOGY: linear (ii) MOLECULE TYPE: cDNA (ix) FEATURE:
            (A) NAME/KEY:
            (B) LOCATION:
            (D) OTHER INFORMATION:

(xi) SEQUENCE DESCRIPTION: SEQ ID NO: 6:

```
GCAGCAGCAA CAACCAGTGC CATAGACACT CTCCATCAAC AAACTCTAGC TGATCAATCC      60

TAGCTAAGCT TATTACATAG CAAGCATGGG GTACTCCAAA ACCCTAGTAG CTGGCCTGTT     120

CGCAATGCTG TTACTAGCTC CGGCCGTCTT GGCCACCGAC CCAGACCCTC TCCAGGACTT     180

CTGTGTCGCC GACCTCGACG GCAAGGCGGT CTCGGTGAAC GGGCACACGT GCAAGCCCAT     240

GTCGGAGGCC GGCGACGACT TCCTCTTCTC GTCCAAGTTG GCCAAGGCCG GCAACACGTC     300

CACCCCGAAC GGCTCCGCCG TGACGGAGCT CGACGTGGCC GAGTGGCCCG GTACCAACAC     360

GCTGGGTGTG TCCATGAACC GCGTGGACTT TGCTCCCGGA GGCACCAACC CACCACACAT     420

CCACCCGCGT GCCACCGAGA TCGGCATCGT GATGAAAGGT GAGCTTCTCG TGGGAATCCT     480

TGGCAGCCTC GACTCGGGA ACAAGCTCTA CTCGAGGGTG GTGCGCGCCG GAGAGACGTT     540

CCTCATCCCA CGGGGCCTCA TGCACTTCCA GTTCAACGTC GGTAAGACCG AGGCCTCCAT     600

GGTCGTCTCC TTCAACAGCC AGAACCCCGG CATTGTCTTC GTGCCCCTCA CGCTCTTCGG     660

CTCCAACCCG CCCATCCCAA CGCCGGTGCT CACCAAGGCA CTCCGGGTGG AGGCCAGGGT     720

CGTGGAACTT CTCAAGTCCA AGTTTGCCGC TGGGTTTTAA TTTCTAGGAG CCTTCCCTGA     780

AATGATAATT ATATAATTCC ATATATGCAT GCTAGCAAAA TTTAATAATT CTCACCAGAA     840

GACATGTATT CAAGTTTCAG GTTAATCTCG CATGTAGTCG TGTAATAAGA TTGAACAAGT     900

TAGCCTCATG GTGTAGCCTT CGATCAGAAC CAATATGAGG AATTGAATGT ACTACTTTTT     960

ATTGTCGTCT TTGTTCTTTT CACTGAACGG AATATATAAT AAGCATTTTC GTAAAAAAAA    1020

AAAAAAAAAA AAAAAAAAAA AAAAAAAAAA AAAAAAAAAA AAAAAAAAAA AAAAA         1075
```